(12) United States Patent
Derchak et al.

(10) Patent No.: US 9,526,419 B2
(45) Date of Patent: Dec. 27, 2016

(54) GARMENT FOR PHYSIOLOGICAL CHARACTERISTICS MONITORING

(75) Inventors: P. Alexander Derchak, Oxnard, CA (US); Larry James Czapla, Coto de Caza, CA (US)

(73) Assignee: adidas AG, Herzogenaurach (DE)

( * ) Notice: Subject to any disclaimer, the term of this patent is extended or adjusted under 35 U.S.C. 154(b) by 554 days.

(21) Appl. No.: 12/869,578

(22) Filed: Aug. 26, 2010

(65) Prior Publication Data

US 2011/0054271 A1 Mar. 3, 2011

Related U.S. Application Data

(60) Provisional application No. 61/275,574, filed on Sep. 1, 2009.

(51) Int. Cl.
| | |
|---|---|
| A61B 5/00 | (2006.01) |
| A61B 5/113 | (2006.01) |
| A61B 5/0205 | (2006.01) |
| A61B 5/024 | (2006.01) |
| A61B 5/0402 | (2006.01) |
| A61B 5/0476 | (2006.01) |
| A61B 5/11 | (2006.01) |

(Continued)

(52) U.S. Cl.
CPC ........... *A61B 5/0002* (2013.01); *A61B 5/1135* (2013.01); *A61B 5/6805* (2013.01); *A61B 5/02055* (2013.01); *A61B 5/02438* (2013.01); *A61B 5/0402* (2013.01); *A61B 5/0476* (2013.01); *A61B 5/11* (2013.01); *A61B 5/14551* (2013.01); *A61B 5/411* (2013.01); *A61B 2562/0219* (2013.01); *G06F 19/3481* (2013.01)

(58) Field of Classification Search
CPC ............... A61B 5/0002; A61B 2562/0223; A61B 2562/0219; A61B 5/6805; A61B 5/02438
USPC ......................... 600/301, 534, 409
See application file for complete search history.

(56) References Cited

U.S. PATENT DOCUMENTS

| | | |
|---|---|---|
| 3,831,586 A | 8/1974 | Petit |
| 4,033,332 A | 7/1977 | Hardway et al. |
| 4,258,718 A | 3/1981 | Goldman |

(Continued)

FOREIGN PATENT DOCUMENTS

| | | |
|---|---|---|
| JP | 3-501554 A | 4/1991 |
| JP | 5-91511 A | 4/1993 |

(Continued)

OTHER PUBLICATIONS

McCool et al. (Tidal Volume and Respiratory Timing Derived from a portable Ventilation Monitor, Chest, 2002; 122:684-691).*

(Continued)

*Primary Examiner* — Serkan Akar
(74) *Attorney, Agent, or Firm* — Sterne, Kessler, Goldstein & Fox P.L.L.C.

(57) ABSTRACT

Monitoring systems for noninvasively monitoring physiological parameters of a subject, including (i) a wearable monitoring garment adapted to cover at least a portion of a subject's torso, and (ii) a magnetometer system that is embedded in the monitoring garment, the magnetometer system including at least paired first transmission and receiver magnetometers and paired second transmission and receiver magnetometers, the magnetometer system being responsive to changes in distance between the paired magnetometers.

19 Claims, 3 Drawing Sheets

(51) Int. Cl.
*A61B 5/1455* (2006.01)
*G06F 19/00* (2011.01)

(56) References Cited

U.S. PATENT DOCUMENTS

| | | | |
|---|---|---|---|
| 4,267,845 A | 5/1981 | Robertson, Jr. et al. | |
| 4,494,553 A | 1/1985 | Sciarra et al. | |
| 5,002,060 A | 3/1991 | Nedivi | |
| 5,148,002 A | 9/1992 | Kuo et al. | |
| 5,255,318 A | 10/1993 | Gurusami et al. | |
| 5,549,113 A | 8/1996 | Halleck et al. | |
| 5,738,102 A | 4/1998 | Lemelson | |
| 5,825,293 A | 10/1998 | Ahmed et al. | |
| 5,906,004 A | 5/1999 | Lebby et al. | |
| 6,015,388 A | 1/2000 | Sackner et al. | |
| 6,047,203 A | 4/2000 | Sackner et al. | |
| 6,080,690 A | 6/2000 | Lebby et al. | |
| 6,198,394 B1 | 3/2001 | Jacobsen et al. | |
| 6,268,725 B1 | 7/2001 | Vernon et al. | |
| 6,341,504 B1 | 1/2002 | Istook | |
| 6,450,957 B1 | 9/2002 | Yoshimi et al. | |
| 6,454,719 B1 | 9/2002 | Greenhut | |
| 6,468,234 B1 | 10/2002 | Van der Loos et al. | |
| 6,517,497 B2 | 2/2003 | Rymut et al. | |
| 6,527,729 B1 | 3/2003 | Turcott | |
| 6,551,252 B2 | 4/2003 | Sackner et al. | |
| 6,599,251 B2 | 7/2003 | Chen et al. | |
| 6,600,949 B1 | 7/2003 | Turcott | |
| 6,727,197 B1 | 4/2004 | Wilson et al. | |
| 6,790,183 B2 | 9/2004 | Murphy | |
| 6,840,907 B1 | 1/2005 | Brydon | |
| 6,858,006 B2 | 2/2005 | MacCarter et al. | |
| 7,267,262 B1 | 9/2007 | Brown | |
| 7,267,652 B2 | 9/2007 | Coyle et al. | |
| 7,295,928 B2 | 11/2007 | Hassan et al. | |
| 2002/0123701 A1 | 9/2002 | Eriksen et al. | |
| 2004/0097823 A1 | 5/2004 | Friedrichs et al. | |
| 2004/0117204 A1 | 6/2004 | Mazar et al. | |
| 2004/0122334 A1 | 6/2004 | Yamashiro | |
| 2004/0133079 A1 | 7/2004 | Mazar | |
| 2005/0054941 A1 | 3/2005 | Ting | |
| 2005/0119586 A1 | 6/2005 | Coyle et al. | |
| 2006/0229058 A1* | 10/2006 | Rosenberg | H04L 67/18 455/404.2 |
| 2007/0169364 A1 | 7/2007 | Townsend et al. | |
| 2008/0039700 A1 | 2/2008 | Drinan et al. | |
| 2008/0045815 A1 | 2/2008 | Derchak et al. | |
| 2008/0082018 A1 | 4/2008 | Sackner et al. | |
| 2008/0223131 A1 | 9/2008 | Vannucci et al. | |
| 2008/0269644 A1 | 10/2008 | Ray | |
| 2009/0047645 A1 | 2/2009 | DiBenedetto et al. | |
| 2010/0027515 A1 | 2/2010 | Hylton | |
| 2010/0234699 A1 | 9/2010 | Lanfermann et al. | |
| 2010/0292050 A1 | 11/2010 | DiBenedetto et al. | |
| 2011/0009766 A1 | 1/2011 | McCool | |
| 2011/0153701 A1 | 6/2011 | Moudgill | |

FOREIGN PATENT DOCUMENTS

| | | |
|---|---|---|
| JP | 09-028661 A | 2/1997 |
| JP | 2003-513260 A | 4/2003 |
| JP | 2005-184188 A | 7/2005 |
| JP | 2006-208291 A | 8/2006 |
| WO | 89/05549 A1 | 6/1989 |
| WO | WO 01/28420 A1 | 4/2001 |
| WO | 01/33162 A1 | 5/2001 |
| WO | WO 01/76467 A2 | 10/2001 |
| WO | WO 2006/009830 A2 | 1/2006 |
| WO | WO 2007/069111 A2 | 6/2007 |
| WO | WO 2009/074973 A1 | 6/2009 |

OTHER PUBLICATIONS

Noury et al. (VTAMN A Smart Clothe for Ambulatory Remote Monitoring of Physiological Parameters and Activity, IEEE EMBS, 2004).*
Clarenbach et al. (Monitoring of Ventilation During Exercise by a Portable Respiratory Inductive Plethysmograph, Chest 2005; 128:1282-1290.*
Angelo et al., "A system for respiratory motion detection using optical fibers embedded into textiles", 30th Annual International IEEE EMBS Conference Vancouver, British Columbia, Canada, Aug. 20-24, 2008, pp. 3694-3697.*
Keenan et al. International Journal of Signal Processing 2;1 Winter 2006.*
Badler, et al., "Simulating Humans: Computer Graphics, Animation, and Control", (New York; Oxford University Press, 1993).
DeCarlo, et al., "Integrating Anatomy and Physiology for Behavior Modeling", Medicine Meets Virtual Reality 3 (San Diego, 1995).
McCool, et al., "Estimates of Ventilation From Body Surface Measurements in Unrestrained Subjects", J. Appl. Physiol., vol. 61, pp. 1114-1119 (1986).
Mead, et al., "Pulmonary Ventilation Measured from Body Surface Movements", Science, pp. 196, 1383-1384 (1967).
Paek, et al., "Postural Effects on Measurements of Tidal Volume From Body Surface Displacements", J. Appl. Physiol., vol. 68, pp. 2482-2487 (1990).
Smith, et al., "Three Degree of Freedom Description of Movement of the Human Chest Wall", J. Appl. Physiol., vol. 60, pp. 928-934 (1986).
Wade, O.L., "Movement of the Thoracic Cage and Diaphragm in Respiration", J. Physiol., pp. 124-193 (1954).
Co-pending U.S. Appl. No. 12/869,582, inventors Derchak et al., filed Aug. 26, 2010.
Co-pending U.S. Appl. No. 12/869,576, inventor Stone, Robert, filed Aug. 26, 2010.
Co-pending U.S. Appl. No. 12/869,585, inventor Derchak, P. Alexander, filed Aug. 26, 2010.
Co-pending U.S. Appl. No. 12/869,592, inventor Derchak, P. Alexander, filed Aug. 26, 2010.
Co-pending U.S. Appl. No. 12/872,174, inventors Derchak et al., filed Aug. 31, 2010.
Co-pending U.S. Appl. No. 12/869,625, inventor Derchak, P. Alexander, filed Aug. 26, 2010.
Co-pending U.S. Appl. No. 12/869,586, inventors Derchak et al., filed Aug. 26, 2010.
Co-pending U.S. Appl. No. 12/836,421, inventors Powch, et al., filed Jul. 14, 2010.
Office Action Mailed Sep. 13, 2012 for U.S. Appl. No. 12/869,582.
Office Action Mailed Sep. 21, 2012 for U.S. Appl. No. 12/869,585.
Office Action mailed Mar. 20, 2013 for U.S. Appl. No. 12/869,582.
Office Action mailed Jan. 14, 2013 for U.S. Appl. No. 12/869,585.
Office Action mailed Sep. 17, 2013 for U.S. Appl. No. 12/869,582.
Office Action mailed Mar. 24, 2014 for U.S. Appl. No. 12/869,585.

* cited by examiner

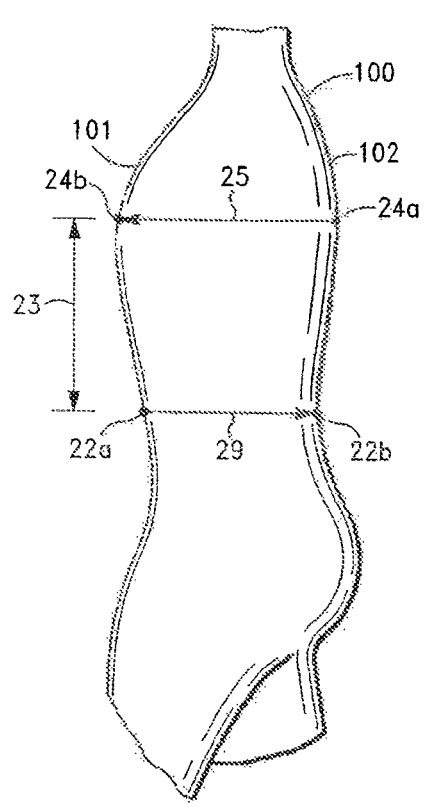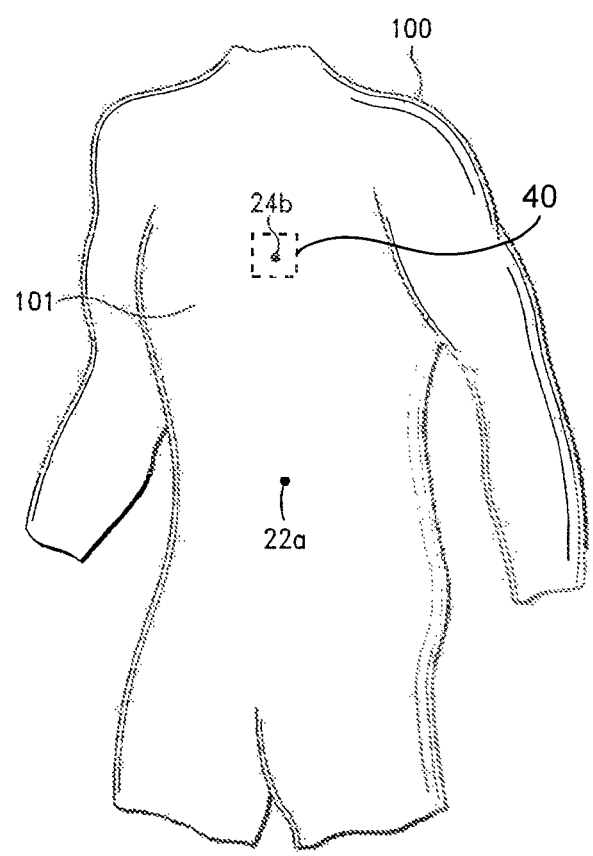
FIG. 3
FIG. 4

GARMENT FOR PHYSIOLOGICAL CHARACTERISTICS MONITORING

CROSS-REFERENCE TO RELATED APPLICATIONS

This non-provisional application claims priority to U.S. Provisional Application No. 61/275,574, filed Sep. 1, 2009, which is incorporated herein by reference in its entirety.

FIELD OF THE INVENTION

The present invention relates generally to methods and systems for monitoring physiological and athletic performance characteristics of a subject. More particularly, the invention relates to improved methods and systems for determining a plurality of physiological and athletic performance characteristics, and characterizing respiratory activity and associated events, as well as spatial parameters, in real time. The methods and systems of the present invention can be applied in a variety of fields, e.g., health care, medical diagnosis and monitoring, and athletic monitoring and coaching.

BACKGROUND OF THE INVENTION

In medical diagnosis and treatment of a subject, it is often necessary to assess one or more physiological characteristics; particularly, respiratory characteristics. A key respiratory characteristic is respiratory air volume (or tidal volume). Respiratory air volume and other respiratory characteristics are also useful to assess athletic performance, for example, by aiding in detection of changes in physiological state and/or performance characteristics.

Monitoring physiological and performance parameters of a subject can be important in planning and evaluating athletic training and activity. A subject may exercise or otherwise engage in athletic activity for a variety of reasons, including, for example, maintaining or achieving a level of fitness, to prepare for or engage in competition, and for enjoyment. The subject may have a training program tailored to his or her fitness level and designed to help him or her progress toward a fitness or exercise goal. Physiological and performance parameters of a subject can provide useful information about the subject's progression in a training program, or about the athletic performance of the subject. In order to accurately appraise the subject's fitness level or progress toward a goal, it may be useful to determine, monitor, and record various physiological or performance parameters, and related contextual information.

Various methods and systems utilizing heart rate have been introduced to approximate effort and physiological stress during exercise. Convenient, practicable, and comfortable means of measuring pulmonary ventilation in non-laboratory conditions, however, have been scarce. While of good value, heart rate can only give an approximation as to the true physiological state of an athlete or medical patient, as it can be confounded by external factors including, for example, sleep levels, caffeine, depressants, beta blockers, stress levels, hydration status, temperature, etc. Furthermore, accurate use of heart rate to gauge physiological performance requires knowledge of the amount of blood flowing to the muscles, which in turn requires knowledge of the instantaneous stroke volume of the heart as well as the rate of pumping. These parameters can be difficult to determine while a subject is engaging in a physical activity.

Various conventional methods and systems have been employed to measure (or determine) tidal volume. One method includes having the patient or subject breathe into a mouthpiece connected to a flow rate measuring device. Flow rate is then integrated to provide air volume change.

As is well known in the art, there are several drawbacks and disadvantages associated with employing a mouthpiece. A significant drawback associated with a mouthpiece and nose-clip measuring device is that the noted items cause changes in the monitored subject's respiratory pattern (i.e., rate and volume). Tidal volume determinations based on a mouthpiece and nose-clip are, thus, often inaccurate.

A mouthpiece is difficult to use for monitoring athletic performance as well as for long term monitoring, especially for ill, sleeping, or anesthetized subjects. It is uncomfortable for the subject, tends to restrict breathing, and is generally inconvenient for the physician or technician to use. Monitoring respiratory characteristics using a mouthpiece is particularly impractical in the athletic performance monitoring context. During athletic activities, the mouthpiece interferes with the athlete's performance. The processing and collection accessories necessary to monitor the breathing patterns captured by the mouthpiece add further bulk to such devices. These systems also typically require an on-duty technician to set up and operate, further complicating their use.

Other conventional devices for determining tidal volume include respiration monitors. Illustrative are the systems disclosed in U.S. Pat. No. 3,831,586, issued Aug. 27, 1974 and U.S. Pat. No. 4,033,332, issued Jul. 5, 1977, each of which is incorporated by reference herein in its entirety.

Although the noted systems eliminate many of the disadvantages associated with a mouthpiece, the systems do not, in general, provide an accurate measurement of tidal volume. Further, the systems are typically only used to signal an attendant when a subject's breathing activity changes sharply or stops.

A further means for determining tidal volume is to measure the change in size (or displacement) of the rib cage and abdomen, as it is well known that lung volume is a function of these two parameters. A number of systems and devices have been employed to measure the change in size (i.e., Δ circumference) of the rib cage and abdomen, including mercury in rubber strain gauges, pneumobelts, respiratory inductive plethysmograph (RIP) belts, and magnetometers. See, D. L. Wade, "*Movements of the Thoracic Cage and Diaphragm in Respiration*", J. Physiol., pp. 124-193 (1954), Mead, et al., "*Pulmonary Ventilation Measured from Body Surface Movements*", Science, pp. 196, 1383-1384 (1967).

RIP belts are a common means employed to measure changes in the cross-sectional areas of the rib cage and abdomen. RIP belts include conductive loops of wire that are coiled and sewed into an elastic belt. As the coil stretches and contracts in response to changes in a subject's chest cavity size, a magnetic field generated by the wire changes. The output voltage of an RIP belt is generally linearly related to changes in the expanded length of the belt and, thus, changes in the enclosed cross-sectional area.

In practice, measuring changes in the cross-sectional areas of the abdomen can increase the accuracy of RIP belt systems. To measure changes in the cross-sectional areas of the rib cage and abdomen, one belt is typically secured around the mid-thorax and a second belt is typically placed around the mid-abdomen.

RIP belts can also be embedded in a garment, such as a shirt or vest, and appropriately positioned therein to measure rib cage and abdominal displacements, and other anatomical and physiological parameters, such as jugular venous pulse, respiration-related intra-plural pressure changes, etc. Illustrative is the VivoMetrics, Inc. LifeShirt® disclosed in U.S. Pat. No. 6,551,252, issued Apr. 22, 2003 and U.S. Pat. No. 6,341,504, issued Jan. 29, 2002, each of which is incorporated by reference herein in its entirety.

There are some drawbacks, however, to many RIP belt systems. For example, RIP belts are expensive in terms of material construction and in terms of the electrical and computing power required to operate them. In addition, the coils are generally large and tight on the chest and therefore can be cumbersome and uncomfortable for the athlete.

Other technologies have been developed in an attempt to monitor respiratory characteristics of a subject while avoiding the drawbacks of RIP belt systems. These technologies generally work on a strain gauge principle and are often textile based. However, such technologies suffer significantly from motion interference that, by and large, renders them useless in athletic training applications where motion is necessarily at a relatively high level.

In an attempt to rectify the drawbacks of the RIP belt and strain gauge systems, various magnetometer systems have been recently developed to measure displacements of the rib cage and abdomen. Respiratory magnetometer systems typically comprise one or more tuned pairs of air-core magnetometers or electromagnetic coils. Other types of magnetometers sensitive to changes in distance therebetween can also be used. One magnetometer is adapted to transmit a specific high frequency AC magnetic field and the other magnetometer is adapted to receive the field. The paired magnetometers are responsive to changes in a spaced distance therebetween; the changes being reflected in changes in the strength of the magnetic field.

To measure changes in (or displacement of) the anteroposterior diameter of the rib cage, a first magnetometer is typically placed over the sternum at the level of the 4th intercostal space and the second magnetometer is placed over the spine at the same level. Using additional magnetometers can increase the accuracy of the magnetometer system. For example, to measure changes in the anteroposterior diameter of the abdomen, a third magnetometer can be placed on the abdomen at the level of the umbilicus and a fourth magnetometer can be placed over the spine at the same level.

Over the operational range of distances, the output voltage is linearly related to the distance between two magnetometers provided that the axes of the magnetometers remain substantially parallel to each other. As rotation of the axes can change the voltage, the magnetometers are typically secured to the subject's skin in a parallel fashion and rotation due to the motion of underlying soft tissue is minimized.

As set forth herein, magnetometers can also be embedded in or carried by a wearable garment, such as a shirt or vest. The wearable monitoring garment eliminates the need to attach the magnetometers directly to the skin of a subject and, hence, resolves all issues related thereto. The wearable monitoring garment also facilitates repeated and convenient positioning of magnetometers at virtually any appropriate (or desired) position on a subject's torso.

Various methods, algorithms, and mathematical models have been employed with the aforementioned systems to determine tidal volume and other respiratory characteristics. In practice, "two-degrees-of-freedom" models are typically employed to determine tidal volume from RIP belt-derived rib cage and abdominal displacements.

The "two-degrees-of-freedom" models are premised on the inter-related movements by and between the thoracic cavity and the anterior and lateral walls of the rib cage and the abdomen, i.e., since the first rib and adjacent structures of the neck are relatively immobile, the moveable components of the thoracic cavity are taken to be the anterior and lateral walls of the rib cage and the abdomen. Changes in volume of the thoracic cavity will then be reflected by displacements of the rib cage and abdomen.

As is well known in the art, displacement (i.e., movement) of the rib cage can be directly assessed with an RIP belt. Diaphragm displacement cannot, however, be measured directly. But, since the abdominal contents are essentially incompressible, caudal motion of the diaphragm relative to the pelvis and the volume it displaces is reflected by outward movement of the anterolateral abdominal wall.

The "two-degrees-of-freedom" model embraced by many in the field holds that tidal volume ($V_T$) is equal to the sum of the volume displacements of the rib cage and abdomen, i.e.:

$$V_T = \alpha RC + \beta Ab \qquad \text{Eq. 1}$$

where RC and Ab represent linear displacements of the rib cage and abdomen, respectively, and $\alpha$ and $\beta$ represent volume-motion coefficients.

The accuracy of the "two-degrees-of-freedom" model and, hence, methods employing same to determine volume-motion coefficients of the rib cage and abdomen, is limited by virtue of changes in spinal flexion that can accompany changes in posture. It has been found that $V_T$ can be over or under-estimated by as much as 50% of the vital capacity with spinal flexion and extension. See, McCool, et al., "*Estimates of Ventilation From Body Surface Measurements in Unrestrained Subjects*", J. Appl. Physiol., vol. 61, pp. 1114-1119 (1986) and Paek, et al., "*Postural Effects on Measurements of Tidal Volume From Body Surface Displacements*", J. Appl. Physiol., vol. 68, pp. 2482-2487 (1990).

There are two major causes that contribute to the noted error and, hence, limitation. A first contributing cause of the error is due to the substantial displacement of the summed rib cage and abdomen signals that occurs with isovolume spinal flexion and extension or pelvic rotation.

The second contributing cause of the error is due to posturally-induced changes in volume-motion coefficients. With isovolume spinal flexion, the rib cage comes down with respect to the pelvis and the axial dimension of the anterior abdominal wall becomes smaller. Therefore, less abdominal cavity is bordered by the anterior abdominal wall.

With a smaller anterior abdominal wall surface to displace, a given volume displacement of the abdominal compartment would be accompanied by a greater outward displacement of the anterior abdominal wall. The abdominal volume-motion coefficient would accordingly be reduced.

It has, however, been found that the addition of a measure of the axial motion of the chest wall e.g., changes in the distance between the xiphoid and the pubic symphysis (Xi), provides a third degree of freedom, which, when employed to determine tidal volume ($V_T$) can reduce the posture related error associated with the "two-degrees-of-freedom" model to within 15% of that measured by spirometry. See, Paek, et al., "*Postural Effects on Measurements of Tidal Volume From Body Surface Displacements*", J. Appl. Physiol., vol. 68, pp. 2482-2487 (1990); and Smith, et al., "*Three Degree of Freedom Description of Movement of the Human Chest Wall*", J. Appl. Physiol., Vol. 60, pp. 928-934 (1986).

Several magnetometer systems are thus adapted to additionally measure the displacement of the chest wall. Illustrative are the magnetometer systems disclosed in co-pending U.S. patent application Ser. No. 12/231,692, filed Sep. 5, 2008, which is incorporated by reference herein in its entirety.

Various methods, algorithms and models are similarly employed with the magnetometer systems to determine tidal volume ($V_T$) and other respiratory characteristics based on measured displacements of the rib cage, abdomen, and chest wall. The model embraced by many in the field is set forth in Equation 2 below:

$$V_T = \alpha(\Delta RC) + \beta(\Delta Ab) + \gamma(\Delta Xi) \qquad \text{Eq. 2}$$

where:
ΔRC represents the linear displacement of the rib cage;
ΔAb represents the linear displacement of the abdomen;
ΔXi represents axial displacement of the chest wall;
α represents a rib cage volume-motion coefficient;
β represents an abdominal volume-motion coefficient; and
γ represents a chest wall volume-motion coefficient.

There are, however, similarly several drawbacks and disadvantages associated with the noted "three-degrees-of-freedom" model. A major drawback is that posture related errors in tidal volume determinations are highly probable when a subject is involved in freely moving postural tasks, e.g., bending, wherein spinal flexion and/or extension is exhibited.

The most pronounced effect of spinal flexion is on the abdominal volume-motion coefficient (β). With bending, β decreases as the xiphi-umbilical distance decreases.

Various approaches and models have thus been developed to address the noted dependency and, hence, enhance the accuracy of tidal volume ($V_T$) determinations. In co-pending U.S. patent application Ser. No. 12/231,692, a modified "three-degrees-of-freedom" model is employed to address the dependence of β on the xiphi-umbilical distance, i.e.:

$$V_T = \alpha(\Delta RC) + (\beta_u + \epsilon Xi) \times (\Delta Ab) + \gamma(\Delta Xi) \qquad \text{Eq. 3}$$

where:
ΔRC represents the linear displacement of the rib cage;
ΔAb represents the linear displacement of the abdomen;
ΔXi represents the change in the xiphi-umbilical distance from an upright position;
α represents a rib cage volume-motion coefficient;
β represents an abdominal volume-motion coefficient;
$\beta_u$ represents the value of the abdominal volume-motion coefficient (β) in the upright position;
ϵ represents the linear slope of the relationship of β as a function of the xiphi-umbilical distance Xi;
($B_u + \epsilon Xi$) represents the corrected abdominal volume-motion coefficient; and
γ represents a xiphi-umbilical volume-motion coefficient.

The "three-degrees-of-freedom" model reflected in Equation 3 above and the associated magnetometer systems and methods disclosed in co-pending U.S. patent application Ser. No. 12/231,692 have been found to reduce the posture related error(s) in tidal volume ($V_T$) and other respiratory characteristic determinations. There are, however, several issues with the disclosed magnetometer systems and methods.

One issue is the placement of the coils or magnetometers. As indicated above, to maintain the desired parallel orientation of the paired coils, the coils are typically secured to a subject's skin. As will readily be appreciated by one having ordinary skill in the art, attaching coils or other magnetometers (or medical equipment) directly to the skin of a subject posses several potential problems. Among the problems are subject discomfort, subject sensitivity to the attaching medium (e.g., adhesive, tape, etc.) dislodgement of the coils or magnetometers, and dependence on the practitioner or technician to accurately position the coils and/or magnetometers on the subject.

Another issue is that ambulatory monitoring of respiratory and other physiological characteristics with the disclosed magnetometer systems can, and in many instances, be challenging.

BRIEF SUMMARY OF THE INVENTION

The present invention provides apparatuses and methods for improved monitoring of a subject's respiratory characteristics, which is of particular use in the fields of athletic performance monitoring and medical evaluation. The monitoring system for noninvasively monitoring physiological parameters of a subject, in accordance with one embodiment of the invention, generally comprises (i) a wearable monitoring garment that is adapted to cover at least a portion of a subject's torso, and (ii) a magnetometer system, the magnetometer system being embedded in the monitoring garment, the magnetometer system including magnetometers that are responsive to changes in distance therebetween, the magnetometer system being adapted to generate at least one signal representing changes in the distance between the magnetometers. A variety of magnetometer types can be used in the magnetomer system, for example, coils or magnets.

In some embodiments of the invention, the monitoring system includes at least one physiological sensor system adapted to detect at least one physiological characteristic associated with the subject. For example, accelerometers, global positioning systems (GPS), and/or other orientation or movement monitoring devices can be included in the monitoring system to provide additional information regarding the subject's physiological state. In some embodiments of the invention, the physiological sensor system is also embedded in the wearable monitoring garment.

In accordance with another embodiment, there is provided a monitoring system for noninvasively monitoring physiological parameters of a subject, comprising (i) a wearable monitoring garment adapted to cover at least a portion of a subject's torso, and (ii) a magnetometer system including a first magnetometer and a second magnetometer, the magnetometer system being embedded in the monitoring garment, wherein the first magnetometer is configured to transmit a signal and the second magnetometer is configured to receive a signal from the first magnetometer. One of the first and second magnetometers can be positioned on the front of the subject, preferably in an area corresponding to the subject's ribcage. The other of the first and second magnetometers can be positioned on the back of the subject, generally in the same plane as the magnetometer on the front of the subject. The first magnetometer can be adapted to generate a first magnetic field from a first position of the monitoring garment (e.g., the subject's chest area) and the second magnetometer can be adapted to receive the first magnetic field from a second position of the monitoring garment (e.g., the subject's upper back). The magnetometer system is responsive to changes in distance between the first magnetometer and second magnetometer.

The magnetometer system can also include additional magnetometers. For example, the magnetometer system can include third and fourth magnetometers, wherein the third magnetometer is configured to transmit a signal and the fourth magnetometer is configured to receive a signal from the third magnetometer. The third magnetometer can be adapted to generate a second magnetic field from a third position of the monitoring garment (e.g., the subjects abdomen). The fourth magnetometer can be adapted to receive the first magnetic field from the first magnetometer and the second magnetic field from the third magnetometer. The fourth magnetometer can be located at a fourth position of the monitoring garment, (e.g., a position corresponding to the subject's middle or lower back). When the third and fourth magnetometers are included in the magnetometer system, the magnetometer system can be responsive to changes in distance between the third and fourth magnetometers and, in some embodiments, changes in distance between the first and fourth magnetometers. The magnetometer system can be further adapted to generate and transmit a first signal representing a change in the distance between the first and second magnetometers, at least a second signal representing a change in distance between the third and fourth magnetometers, and at least a third signal representing a change in distance between the first and fourth magnetometers. It is understood that more or less than four magnetometers can be used in embodiments of the present invention.

In some embodiments of the invention, when the monitoring garment is worn by the subject, the first magnetometer position is proximate the subject's abdomen and the second magnetometer position is on the back of the subject proximate the same axial plane of the first magnetometer position, and the fourth magnetometer position is on the front of the subject proximate the base of the subject's sternum and the third magnetometer position is on the back of the subject proximate the same axial plane of the fourth magnetometer position, whereby the first signal represents the displacement of the subject's abdominal region, the second signal represents the displacement of the subject's rib cage, and the third signal represents the displacement of the subject's chest wall.

In one embodiment, the monitoring system includes processor means for processing the first, second and third signals, and transmission means for transmitting the first, second and third signals from the magnetometer system to the processor means.

In one embodiment, the processor means is also embedded in the monitoring garment.

In one embodiment, the transmission means includes a wireless communication link and associated protocol.

In some embodiments, other sensors can be included in the monitoring system. For example, heart rate monitors, accelerometers to detect movement and speed of a subject, global positioning systems (GPS), and/or other orientation or movement monitoring devices can be included in the monitoring system to provide additional information regarding the subject's physiological state.

BRIEF DESCRIPTION OF THE FIGURES

Further features and advantages will become apparent from the following and more particular description of the present invention, as illustrated in the accompanying drawings, and in which like referenced characters generally refer to the same parts or elements throughout the views.

FIG. 3 is a side view of a subject, showing the position of the dual-paired electromagnetic coil arrangement of FIG. 2 on the subject, according to one embodiment of the invention.

FIG. 4 is a perspective view of the subject, showing the position of electromagnetic coils on the front of the subject, according to one embodiment of the invention.

DETAILED DESCRIPTION OF THE INVENTION

Figure 1:
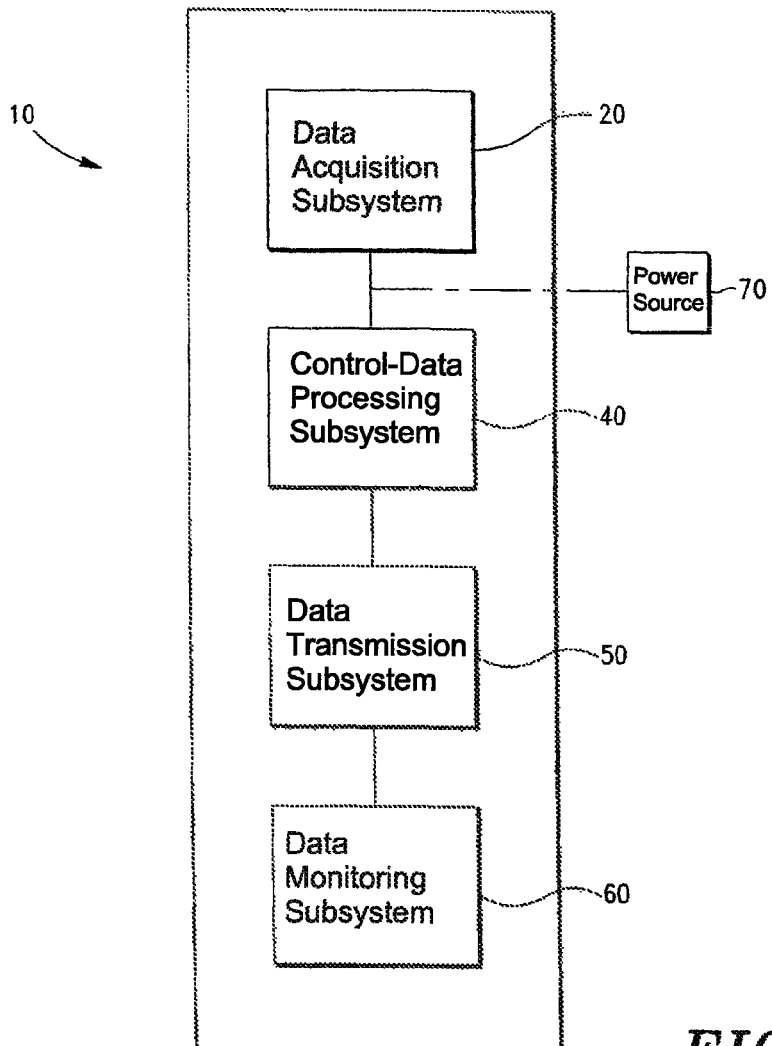
FIG. 1 is a schematic illustration of a physiology monitoring system, according to one embodiment of the invention.

Before describing the present invention in detail, it is to be understood that this invention is not limited to particularly exemplified methods, apparatuses, systems, or circuits, as such may, of course, vary. Thus, although a number of methods and systems similar or equivalent to those described herein can be used in the practice of the present invention, the preferred methods, apparatus and systems are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

As used in this specification and the appended claims, the singular forms "a", "an", and "the" include plural referents unless the content clearly dictates otherwise.

Further, all publications, patents, and patent applications cited herein, whether supra or infra, are hereby incorporated by reference in their entirety.

The publications discussed herein are provided solely for their disclosure prior to the filing date of the present application. Nothing herein is to be construed as an admission that the present invention is not entitled to antedate such publication(s) by virtue of prior invention. Further, the dates of publication may be different from the actual publication dates, which may need to be independently confirmed.

Definitions

The terms "respiratory parameter" and "respiratory characteristic", as used herein, mean and include a characteristic associated with the respiratory system and functioning thereof, including, without limitation, breathing frequency (fB), tidal volume ($V_T$), inspiration volume ($V_I$), expiration volume ($V_E$), minute ventilation (VE), inspiratory breathing time, expiratory breathing time, and flow rates (e.g., rates of change in the chest wall volume). The terms "respiratory parameter" and "respiratory characteristic" further mean and include inferences regarding ventilatory mechanics from synchronous or asynchronous movements of the chest wall compartments.

According to the present invention, flow rates and respiratory accelerations can be determined from a volume signal. Further, numerous inferences regarding ventilatory mechanics can be drawn from the degree of asynchrony in movement occurring amongst the discrete compartments that make up the chest wall.

The terms "respiratory system disorder", "respiratory disorder", and "adverse respiratory event", as used herein, mean and include any dysfunction of the respiratory system that impedes the normal respiration or ventilation process.

The terms "physiological parameter" and "physiological characteristic", as used herein, mean and include, without limitation, electrical activity of the heart, electrical activity of other muscles, electrical activity of the brain, pulse rate, blood pressure, blood oxygen saturation level, skin temperature, and core temperature.

The terms "spatial parameter" and "spatial characteristic", as used herein, mean and include a subject's orientation and/or movement.

The terms "patient" and "subject", as used herein, mean and include humans and animals.

Pulmonary ventilation, tidal volume, respiratory rate, and other associated respiratory characteristics can provide a reliable and practical measure of oxygen and carbon dioxide transpiration in a living body. Respiratory characteristics are directly connected to exercise effort, physiological stress, and other physiological characteristics. One way to externally determine tidal volume is to measure the change in thoracic volume. Change in thoracic volume is caused by the expansion and contraction of the lungs. As the gas pressure in the lungs at the maxima and minima of the pressure ranges is equilibrated to surrounding air pressure, there is a very close and monotonic relationship between the volume of the lungs and the volume of air inspired.

Accurate measurement of the change in thoracic volume involves measuring the change in the diameter of the chest at the ribcage. Measurement of the change in the diameter of the chest below the ribcage can provide additional accuracy to the measurement. Monitoring changes in the diameter of the chest below the ribcage can account for diaphragm delivered breathing where the contraction and relaxation of the diaphragm muscle causes the organs of the abdomen to be pushed down and outwards, thereby increasing the available volume of the lungs.

Monitoring and analyzing respiratory characteristics can be particularly useful in athletic applications, as there is a direct link between performance and an athlete's processing of oxygen and carbon dioxide. For example, in many athletic training situations, it is helpful to know when the athlete's body transitions between aerobic exercise and anaerobic exercise, sometimes referred to as the athlete's ventilatory threshold. Crossing over the ventilatory threshold level is an indicator of pending performance limitations during sport activities. For example, it can be beneficial for athletes to train in the anaerobic state for limited periods of time. However, for many sports, proper training requires only limited periods of anaerobic exercise interrupted by lower intensity aerobic exercises. It is difficult for an athlete to determine which state, anaerobic or aerobic, he or she is in without referencing physiological characteristics such as respiratory characteristics. Therefore, respiratory monitoring and data processing can provide substantial benefits in athletic training by allowing for accurate and substantially instantaneous measurements of the athlete's exercise state. Changes in an athlete's ventilatory threshold over time, as well as patterns of tidal volume during post-exercise recovery, can be valuable to measure improvements in the athlete's fitness level over the course of a training regime. Respiratory monitoring can further allow for monitoring and analyzing changes in a subject's resting metabolic rate.

A second ventilatory threshold exists at the point when the load on the body is such that the pulmonary ventilation is no longer sufficient to support life sustainably. Dwelling too long in this state will lead to collapse and so determination of this point can be of value in medical applications, and particularly to first responders and other emergency response personnel.

The present invention is directed to noninvasive methods and associated systems for monitoring the physiological status of a subject; particularly, the status of the subject's respiratory system. As discussed in detail below, the monitoring systems of the invention include a wearable monitoring garment having coils or magnetometers embedded in or carried by the wearable garment. In some embodiments, the monitoring systems include additional physiological sensors, such as, for example, temperature sensors and blood oxygen sensors, and processing and monitoring means, which similarly are embedded in or carried by the wearable monitoring garment.

As will readily be appreciated by one having ordinary skill in the art, the wearable monitoring garments of the invention eliminate the need to attach magnetometers (and other physiological sensors) directly to the skin of a subject and, hence, resolve all issues related thereto. The wearable monitoring garments also facilitate repeated and convenient positioning of magnetometers at virtually any appropriate (or desired) position on a subject's torso.

The monitoring systems and methods also accommodate ambulatory monitoring of a subject and provide accurate, real-time determination of a plurality of respiratory and other physiological parameters and characteristics.

Several embodiments of the physiology monitoring systems and associated methods of the invention will now be described in detail. It is understood that the invention is not limited to the systems and associated methods described herein. Indeed, as will be appreciated by one having ordinary skill in the art, systems and associated methods similar or equivalent to the described systems and methods can also be employed within the scope of the present invention.

Further, although the physiology monitoring systems and associated methods are described herein in connection with monitoring physiological parameters and characteristics in a human body, the invention is in no way limited to such use. The physiology monitoring systems and associated methods of the invention can also be employed to monitor physiological parameters in non-human bodies. The physiology monitoring systems and associated methods of the invention can also be employed in non-medical contexts, such as determining volumes and/or volume changes in extensible bladders used for containing liquids and/or gasses.

Referring first to FIG. 1, there is shown a schematic illustration of an exemplary embodiment of a physiology monitoring system that is adapted to (i) monitor and detect changes in (or displacements of) the anteroposterior diameters of the rib cage and abdomen, and axial displacement of the chest wall, and (ii) determine anatomical and physiological information associated with the monitored subject as a function of the signals reflecting the noted anatomical displacements.

As illustrated in FIG. 1, the physiology monitoring system 10 preferably includes a data acquisition subsystem 20, a control-data processing subsystem 40, a data transmission subsystem 50, a data monitoring subsystem 60, and a power source 70, such as a battery.

Figure 2:
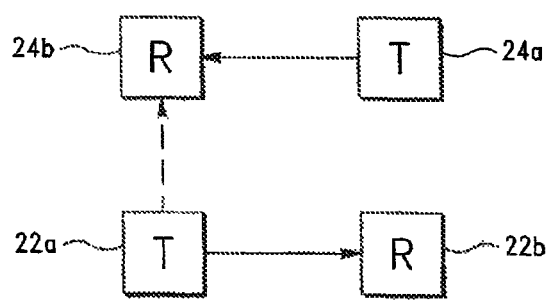
FIG. 2 is a schematic illustration of a dual-paired electromagnetic coil arrangement, according to one embodiment of the invention.

As set forth in FIGS. 2 and 3, the data acquisition subsystem 20 can include paired magnetometers that are positioned on a subject 100 and adapted to monitor and detect changes in (or displacements of) the anteroposterior diameters of the rib cage and abdomen, and axial displacement of the chest wall. As illustrated in FIG. 2, the magnetometers include first transmission magnetometer 22a, first receive magnetometer 22b, second transmission magnetometer 24a, and second receive magnetometer 24b.

Although the present invention is described herein in terms of magnetometers and magnetometer systems, it is understood that other types of sensor systems capable of measuring changes in distance between two or more sensors in the system can be used in place of, or in addition to, magnetometers. Specifically, the invention is not limited to the use of electromagnetic coils or magnetometers to acquire signals representing measured changes in the anteroposterior diameters of the rib cage and abdomen, and axial displacement of the chest wall. Various additional means and devices that can be readily adapted to measure the noted anatomical parameters can be employed within the scope of the invention. Such means and devices include, without limitation, Hall effect sensors and electronic compass sensors. Wireless sensors with the capability of measuring time delay in a signal sent from one sensor to another and thereby determine the distance between the two sensors can be substituted for or provided in addition to magnetometers in accordance with the present invention.

Control-data processing subsystem 40 includes programs, instructions and associated algorithms and parameters to control data acquisition subsystem 20 and, hence, the paired magnetometers and the function thereof, and the transmission and receipt of signals, as well as data transmission subsystem 50 and data monitoring subsystem 60.

Control-data processing subsystem 40 is further programmed and adapted to retrieve and process transmissions or signals reflecting changes in the magnetometer fields (and, hence, changes in spaced distances between the paired magnetometers) and to determine anatomical and physiological information associated with the monitored subject (as a function of the signals), including at least one respiratory characteristic (more preferably, a plurality of respiratory characteristics). Control-data processing subsystem 40 is also referred to herein as "processor subsystem," "processing subsystem," and "data processing subsystem." The terms control-data processing subsystem, processor subsystem, processing subsystem, and data processing subsystem are used interchangeably in the present application.

Data monitoring subsystem 60 is designed and adapted to display physiological and performance characteristics and parameters generated and transmitted by control-data processing subsystem 40.

Data transmission subsystem 50 is programmed and adapted to monitor and control the communication links and, hence, transmissions by and between data acquisition subsystem 20, control-data processing subsystem 40, and data monitoring subsystem 60.

Further details of the noted physiological monitoring system are set forth in U.S. Provisional Application No. 61/275,575, filed Sep. 1, 2009, and co-pending U.S. application Ser. No. 12/869,582, filed Aug. 26, 2010, each of which is incorporated by reference herein in its entirety.

Figure 5:
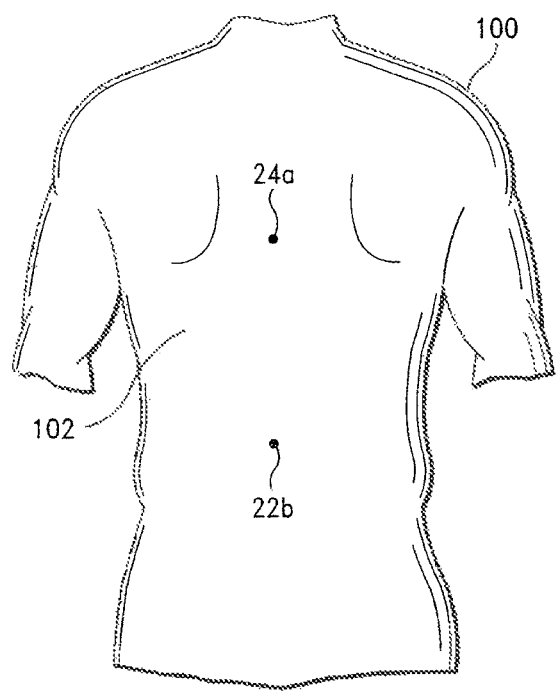
FIG. 5 is a plane view of the subject's back, showing the position of electromagnetic coils thereon, according to one embodiment of the invention.

As will be readily appreciated by one having ordinary skill in the art, the paired magnetometers can be disposed in various anatomically appropriate positions on a subject to monitor and measure the change in distance (or displacement) between the magnetometers. Referring now to FIGS. 3-5, there is shown the position of magnetometers 22a, 22b, 24a, 24b on a subject or patient 100, in accordance with the inventions disclosed in U.S. Provisional Application No. 61/275,575, co-pending U.S. application Ser. No. 12/869, 582, and co-pending U.S. patent application Ser. No. 12/231, 692, filed Sep. 5, 2008, each of which is incorporated by reference herein in its entirety.

As illustrated in FIGS. 3-5, first transmission magnetometer (i.e., first transmitter) 22a is preferably positioned on front 101 of subject 100 proximate the subject's umbilicus, and first receive magnetometer (i.e., first receiver) 22b is preferably positioned proximate the same axial position, but on back 102 of subject 100. Second receive magnetometer (i.e., second receiver) 24b is preferably positioned on front 101 of subject 100 proximate the base of the sternum, and second transmission magnetometer (i.e., second transmitter) 24a is positioned proximate the same axial position, but on back 102 of subject 100.

As the subject or patient 100 breathes, displacement(s) of the rib cage and abdomen (i.e., changes in the distance between paired magnetometers 22a, 22b and 24a, 24b, denoted, respectively, by arrow 29 and arrow 25), is determined from measured changes in the magnetic field between paired magnetometers 22a, 22b and 24a, 24b. The axial displacement of the chest wall, denoted by arrow 23 (e.g., xiphiumbilical distance (Xi)) is also determined from measured changes in the magnetic field between magnetometers 22a and 24b. In such a case, magnetometer 24b can be a dual-function electromagnetic coil, where "dual function" refers to a coil capable of receiving transmissions from a plurality of different transmission coils (i.e., magnetometer 24b is adapted to receive magnetic field transmissions from magnetometers 22a and 24a).

As indicated above, the measured displacements are typically employed to determine anatomical and physiological information associated with the monitored subject, including at least one or more respiratory characteristics. As set forth in U.S. Provisional Application No. 61/275,575, and co-pending U.S. application Ser. No. 12/869,582, additional paired magnetometers can also be employed, and the multiple measured displacements can be employed to assess additional anatomical and physiological characteristics, such as determining and characterizing the relationship(s) of chest wall movement(s) to respiratory activity and respiratory associated events, such as speaking, sneezing, laughing, and coughing.

As also set forth in U.S. Provisional Application No. 61/275,575, and co-pending U.S. application Ser. No. 12/869,582, data acquisition subsystem 20 can additionally include at least one additional physiological sensor (preferably a plurality of additional physiological sensors) adapted to monitor and record one or more physiological characteristics associated with the monitored subject. The physiological sensors can include, without limitation, sensors that are adapted to monitor and record electrical activity of the brain, heart, and other muscles (e.g., EEG, ECG, EMG), pulse rate, blood oxygen saturation level (e.g., $SpO_2$), skin temperature, and core temperature. Physiological parameters measured and/or calculated may include, for example, heart rate, respiration rate, blood oxygen level, blood flow, hydration status, calories burned, muscle fatigue, and/or body temperature.

Exemplary physiological sensors (and associated systems) are disclosed in U.S. Pat. No. 6,551,252, issued Apr. 22, 2003, U.S. Pat. No. 7,267,652, issued Sep. 11, 2007, co-pending U.S. patent application Ser. No. 11/764,527, filed Jun. 18, 2007, and International Application No. PCT/US2005/021433, each of which is incorporated by reference herein in its entirety.

Data acquisition subsystem 20 can also include one or more audio sensors, such as, for example, a microphone, for monitoring sounds generated by a monitored subject, and a speaker to enable two-way communication by and between the monitored subject and a monitoring station or individual.

As indicated above, the monitoring systems of the invention include a wearable monitoring garments that can be comfortably worn by a monitored subject. In a preferred embodiment of the invention, the wearable monitoring garments include coils or magnetometers, which are embedded in or carried by the wearable garment. According to the invention, the wearable monitoring garment can comprise various items that are adapted to cover at least a portion of a subject's body, such as a shirt, vest, jacket, patch, and the like.

In some embodiments of the invention, the aforementioned additional sensors, processing and monitoring systems (e.g., LDUs, if employed) associated wiring, cabling, and other power and signal transmission apparatus and/or systems are similarly embedded in or carried by the wearable garment.

Figure 6:
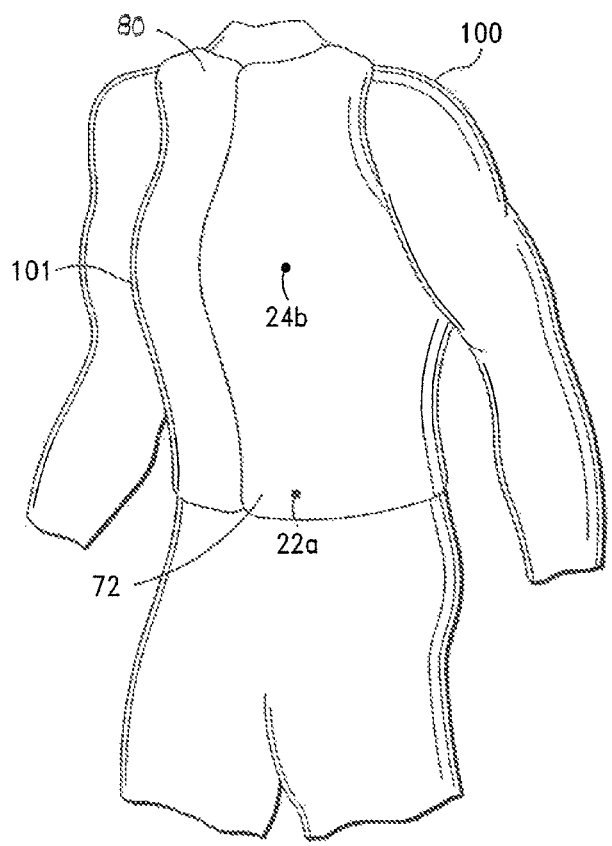
FIG. 6 is an illustration of a wearable monitoring garment, according to one embodiment of the invention.

Referring now to FIG. 6, there is shown one embodiment of a wearable monitoring garment 80 of the invention. As illustrated in FIG. 6, the wearable monitoring garment 80 comprises a sleeveless shirt or vest, having magnetometers (e.g., magnetometers 22a, 24b) associated therewith.

Vest 80 preferably includes an overlapping front portion 72 having closure means that secures vest 80 to the subject's torso. According to the invention, various conventional closure means, such as a hook and pile system, e.g., VELCRO® such as that manufactured by Velcro, Inc., snaps, zipper, etc., can be incorporated into vest 80 to facilitate closure thereof.

Additional suitable garments are also disclosed in U.S. Pat. No. 7,267,652, U.S. Pat. No. 6,551,252, and U.S. Pat. No. 6,047,203, issued Apr. 4, 2000, each of which is incorporated by reference herein in its entirety.

According to the invention, the magnetometers, additional sensors, processing and monitoring systems, and other equipment can be arranged in or carried by the garment, for example, in open or closed pockets, or attached to the garment, for example, as by sewing, gluing, a hook and pile system, e.g., VELCRO® such as that manufactured by Velcro, Inc., and the like. As indicated above, the magnetometers (e.g., magnetometers 22a, 22b, 24a, 24b) and additional sensors, if employed, can be disposed in or carried by the wearable garment at virtually any desired position, whereby, when the garment is worn by a subject the magnetometers and other sensors are positioned proximate any desired position on the subject's body.

The methods and systems of the invention, described above, thus provide numerous significant advantages over conventional physiology monitoring methods and systems. A significant advantage is the provision of physiology monitoring systems and methods that accommodate ambulatory monitoring of respiratory and other physiological parameters and characteristics.

Additional advantages include the provision of physiology monitoring systems and methods that provide (i) accurate, real-time determination of a plurality of respiratory and other physiological parameters and characteristics, and (ii) real-time determination and characterization of a subject's orientation and movement.

Additional advantages and applications of the present invention are apparent with reference to the systems and methods disclosed in U.S. patent application Ser. No. 12/869,582,filed Aug. 26, 2010U.S. patent application Ser. No. 12/869,576, filed Aug. 26, 2010, U.S. patent application Ser. No. 12/869,585, Aug. 26, 2010, U.S. patent application Ser. No. 12/869,592, filed Aug. 26, 2010 U.S. patent application Ser. No. 12/869,627, filed Aug. 26, 2010U.S. patent application Ser. No. 12/869,625 filed Aug. 26, 2010, and U.S. patent application Ser. No. 12/869,586, filed Aug. 26, 2010, each of which is incorporated by reference herein in its entirety.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A monitoring system for noninvasively monitoring parameters of a subject engaged in a physical activity, the system comprising:
a monitoring garment configured to cover a portion of a subject's torso; and
a magnetometer system embedded in the monitoring garment and comprising a first transmission magnetometer, a first receive magnetometer, a second transmission magnetometer, and a second receive magnetometer,
wherein the first transmission magnetometer is configured to generate, at a first position, a first magnetic field,
wherein the first receive magnetometer is configured to receive, at a second position, the first magnetic field,
wherein the second transmission magnetometer is configured to generate, at a third position, a second magnetic field,
wherein the second receive magnetometer is configured to receive, at a fourth position, the first and second magnetic fields,
wherein the first transmission magnetometer, the first receive magnetometer, the second transmission magnetometer, and the second receive magnetometer are embedded in the monitoring garment,
wherein the magnetometer system is responsive to changes in distance between the first and second positions, the third and fourth positions, and the first and fourth positions, and is further configured to generate and transmit a first signal representing, a change in distance between the first and second positions, a second signal representing a change in distance between the third and fourth positions, and a third signal representing a change in distance between the first and fourth positions,
and wherein the monitoring system is configured to process, using a processor system, a plurality of signals to determine a plurality of respiratory parameters in real time including the existence of a hypopnea event, and is configured to generate and transmit performance parameter signals.

2. The monitoring system of claim 1, wherein the monitoring garment comprises a shirt.

3. The monitoring system of claim 2, wherein, when the monitoring garment is worn by the subject, the first position is on the front of the subject proximate the subject's abdomen, the second position is on the back of the subject proximate the same axial plane of the first position, the fourth position is on the front of the subject proximate the base of the subject's sternum, and the third position is on the back of the subject proximate the same axial plane of the fourth position, whereby the first signal represents a displacement of the subject's abdominal region, the second signal represents a displacement of the subject's rib cage, and the third signal represents a displacement of the subject's chest wall.

4. The monitoring system claim 1, further comprising:
a processor system adapted to process the first, second, and third signals; and
a transmission system to transmit the first, second, and third signals from the magnetometer system to the processor system.

5. The monitoring system of claim 1, therein the processor system is adapted to determine at least one respiratory parameter from the firs second, and third signals.

6. The monitoring system of claim 4, wherein the transmission system comprises a wireless communication link and associated protocol.

7. The monitoring system of claim 4, wherein the transmission system comprises a wired transmission network.

8. The monitoring system of claim 1, wherein the processor system and the magnetometer system are carried by the monitoring garment.

9. The monitoring system of claim 2, wherein the shirt is sleeveless.

10. The monitoring system of claim 1, wherein the performance parameter signals detect changes indicating a transition between an aerobic state of a subject and an anaerobic state of the subject.

11. A monitoring system for noninvasively monitoring parameters of a subject engaged in a physical activity, the system comprising:
a shirt configured to cover a portion of a subject's torso:
a magnetometer system embedded in the shirt and comprising a first transmission magnetometer, a first receive magnetometer, a second transmission magnetometer, and a second receive magnetometer;
a physiological sensor system embedded in the shirt and configured to detect a physiological parameter associated with the subject, aid to generate and transmit a physiological parameter signal representing the detected physiological parameter;
a processor system embedded in the shirt; and
a transmission system embedded in the shirt,
wherein the first transmission magnetometer is configured to generate, at a first position, a first magnetic field.
wherein the first receive magnetometer is configured to receive, at a second position, the first magnetic field,
wherein the second transmission magnetometer is configured to generate, at a third position, a second magnetic field,
wherein the second receive magnetometer is configured to receive, at a fourth position, the first and second magnetic fields,
wherein the magnetometer system is responsive to changes in distance between the first and second positions, the third and fourth positions, and the first and fourth positions, and is further configured to generate and transmit a first signal representing a change in distance between the first and second positions, a second signal representing a change in distance between the third and fourth positions, and a third signal representing a change in distance between the first and fourth positions,
wherein the processor system is adapted to determine a respiratory parameter from the first, second, and third signals, and is configured to generate and transmit a respiratory parameter signal including the existence of a hypopnea event representing the respiratory parameter and the physiological parameter signal,
wherein the transmission system is configured to transmit the first, second, and third signals, and the physiological parameter signal, from the magnetometer system and the physiological sensor system to the processor system,
wherein the physiological parameter comprises at least one of blood oxygen level, blood flow, hydration status, calories burned, and muscle fatigue, and wherein the processing system is configured to generate and transmit performance parameter signals.

12. The monitoring system of claim 11, wherein, when the shirt is worn by the subject, the first position is on the, front of the subject proximate the subject's abdomen, the second position is on the back of the subject proximate the same axial plane of the first position, the fourth position is on the front of the subject proximate the base of the subject's sternum, and the third position is on the back of the subject proximate the same axial plane of the fourth position, whereby the first signal represents a displacement of subject's abdominal region, the second signal represents a displacement of the subject's rib cage, and the third signal represents>a displacement of the subject's chest wall.

13. The monitoring system of claim 12, herein the transmission system comprises a wireless communication link.

14. The monitoring system of claim 11, wherein the transmission system comprises a wired transmission network.

15. The monitoring system of claim 11, wherein the shirt is sleeveless.

16. The monitoring system of claim 11, further comprising a monitoring system configured to receive the respiratory parameter and physiological parameter signals from the processor system, and to recognize and display the respiratory parameter represented by the respiratory parameter signal and the physiological parameter represented by the physiological parameter signal.

17. The monitoring system of claim 11, wherein the performance parameter signals detect changes in patterns of tidal volume during post-exercise recover: such that it measures improvements in a subject's fitness level over a course of a training regime.

18. The monitoring system of claim 11, wherein the performance parameter signals detect changes indicating a transition between an aerobic state of a subject and an anaerobic state of the subject.

19. A monitoring system for noninvasively monitoring parameters of a subject engaged in a physical activity, the system comprising:
a monitoring garment configured to cover a portion of a subject's torso; and
a magnetometer system embedded in the monitoring garment and comprising a first transmission magnetometer, a first receive magnetometer, a second transmission magnetometer, and a second receive magnetometer,
wherein the first transmission magnetometer is configured to generate, at a first position, a first magnetic field,
wherein the first receive magnetometer is configured to receive, at a second position, the first magnetic field,
wherein the second transmission magnetometer is configured to generate, at a third position, a second magnetic field,
wherein the second receive magnetometer is configured to receive, at a fourth position, the first and second magnetic fields,
wherein the first transmission magnetometer, the first receive magnetometer, the second transmission magnetometer, and the second receive magnetometer are embedded in the monitoring garment, wherein the magnetometer system is responsive to changes in distance between the first and second positions, the third and fourth positions, and the first and fourth positions, and is further configured to generate and transmit a first signal representing a change in distance between the first and second positions, a second signal representing a change in distance between the third and fourth positions, and a third signal representing a change in distance between the first and fourth positions, wherein the monitoring system is configured to process using a processor system, a plurality of signals to determine a plurality of respiratory parameters in real time including the existence a hypopnea event, and is configured to generate and transmit performance parameter signals to detect changes in patterns of tidal volume during post-exercise recovery, such that it measures improvements in a subject's fitness level over a course of a training regime.

* * * * *